United States Patent [19]

Shutske

[11] Patent Number: 4,624,955
[45] Date of Patent: Nov. 25, 1986

[54] 6H-ISOXAZOLO[3,4-D]PYRAZOLO[3,4-B]PYRIDINES, METHOD FOR THEIR PREPARATION AND USE AS ANXIOLYTIC AGENTS

[75] Inventor: Gregory M. Shutske, Somerset, N.J.

[73] Assignee: Hoechst-Roussel Pharmaceuticals, Somerville, N.J.

[21] Appl. No.: 812,484

[22] Filed: Dec. 23, 1985

[51] Int. Cl.[4] .................. A61K 31/415; C07D 498/14; C07D 498/12
[52] U.S. Cl. ...................................... 514/293; 546/83; 546/119; 546/120
[58] Field of Search .................... 546/83, 119, 120; 514/293

[56]  References Cited

U.S. PATENT DOCUMENTS 3,928,368 12/1975 Hoehn et al. ................... 546/119
3,933,828 1/1976 Kano et al. ....................... 546/83

OTHER PUBLICATIONS

Hoehn, Z. Chem. vol. 10, No. 10, 386–388 (1970).
Hoehn et al., J. Heterocyclic Chem., 9; 235 (1972).
Denzel et al., Arch. Pharm. 309/76, pp. 486–503 (1976).
Shutske, J. Org. Chem. 49, 180–183 (1984).

Primary Examiner—Henry R. Jiles
Assistant Examiner—J. Richter
Attorney, Agent, or Firm—Tatsuya Ikeda

[57]  ABSTRACT

There are disclosed compounds having the formula

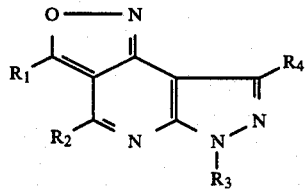

wherein $R_1$ is hydrogen, loweralkyl, arylloweralkyl, aryl or heteroaryl; $R_2$ is hydrogen or loweralkyl; $R_3$ is loweralkyl, loweralkoxyloweralkyl, cycloalkyl, arylloweralkyl or heteroarylmethyl; and $R_4$ is hydrogen or loweralkyl; or a pharmaceutically acceptable acid addition salt thereof, which are useful as anxiolytic agents, methods for synthesizing them, and pharmaceutical compositions comprising an effective amount of such a compound.

29 Claims, No Drawings

6H-ISOXAZOLO[3,4-D]PYRAZOLO[3,4-B]PYRIDINES, METHOD FOR THEIR PREPARATION AND USE AS ANXIOLYTIC AGENTS

This invention relates to compounds having the formula

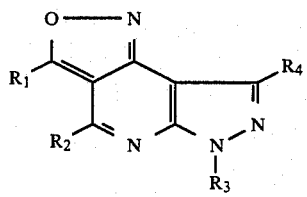

wherein $R_1$ is hydrogen, loweralkyl, arylloweralkyl, aryl or heteroaryl; $R_2$ is hydrogen or loweralkyl; $R_3$ is loweralkyl, loweralkoxyloweralkyl, cycloalkyl, arylloweralkyl or heteroarylmethyl; and $R_4$ is hydrogen or loweralkyl; or a pharmaceutically acceptable acid addition salt thereof, which are useful as anxiolytic, methods for synthesizing them, and pharmaceutical compositions comprising an effective amount of such a compound.

Throughout the specification and the appended claims, a given chemical formula or name shall encompass all stereo and optical isomers thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

Unless otherwise stated or indicted, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term cycloalkyl shall mean a cycloalkyl group of 3 to 7 carbon atoms.

Unless otherwise stated or indicated, the term halogen shall mean fluorine, chlorine, bromine or iodine.

Unless otherwise stated or indicated, the term aryl shall mean an unsubstituted phenyl group or a phenyl group substituted with 1, 2 or 3 substituents each of which being independently a loweralkyl group, loweralkoxy group, hydroxy group, trifluoromethyl group, chlorine or fluorine, with the proviso that the aryl group shall not have chlorine or fluorine at the ortho position.

Unless otherwise stated or indicated, the term heteroaryl group shall mean a group having the formula

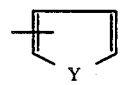

where Y is O, S, $NR_5$ or CH=N, $R_5$ being hydrogen, loweralkyl or phenylloweralkyl, and it shall include all the positional isomers. Thus, for instance, the term shall include both 2-furyl and 3-furyl.

The compounds of this invention are prepared by utilizing one or more of the steps described below.

Throughout the description of the synthetic steps, the notations $R_1$, $R_2$, $R_3$, $R_4$, $R_5$ and Y shall have the respective meanings given above unless otherwise stated or indicated.

Preferred synthetic steps used for synthesizing the compounds of this invention are schematically shown in FIG. 1. It should be understood however, that FIG. 1 is merely a schematic representation presented for the purpose of illustration and it should not be construed too narrowly.

For details of the reaction steps used for preparing compound III depicted in FIG. 1, the reader is referred to H. Hoehn, Th. Denzel and W. Jansen, J. Heterocyclic Chem. 9, 235 (1972), except that in this invention a low temperature (about −75° C. to −40° C.) Grignard reaction was used for the last step as shown in FIG. 1, whereas Hoehn et al. used a cadmium-Grignard reagent at a higher temperature.

FIG. 1 - Reaction Scheme
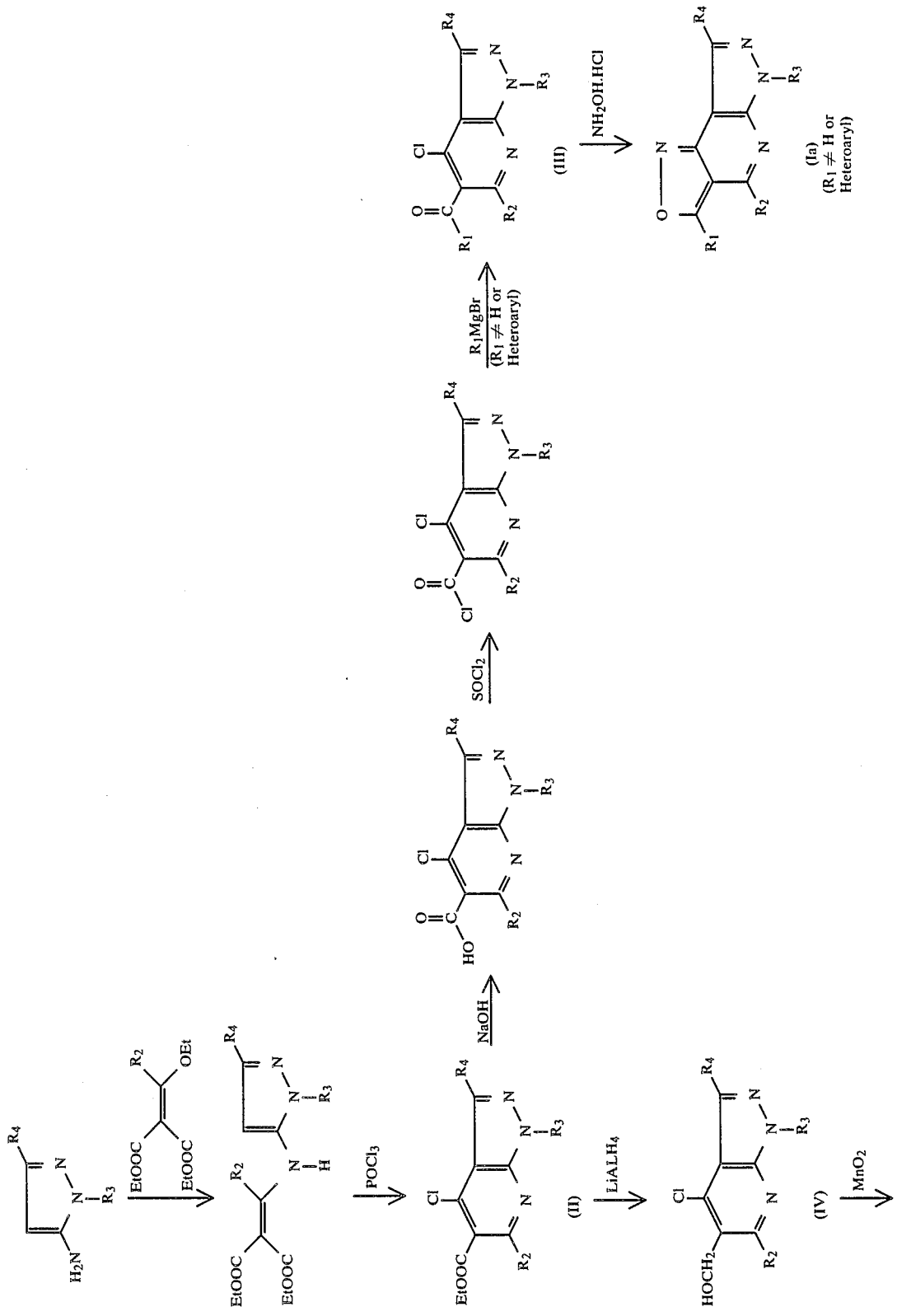

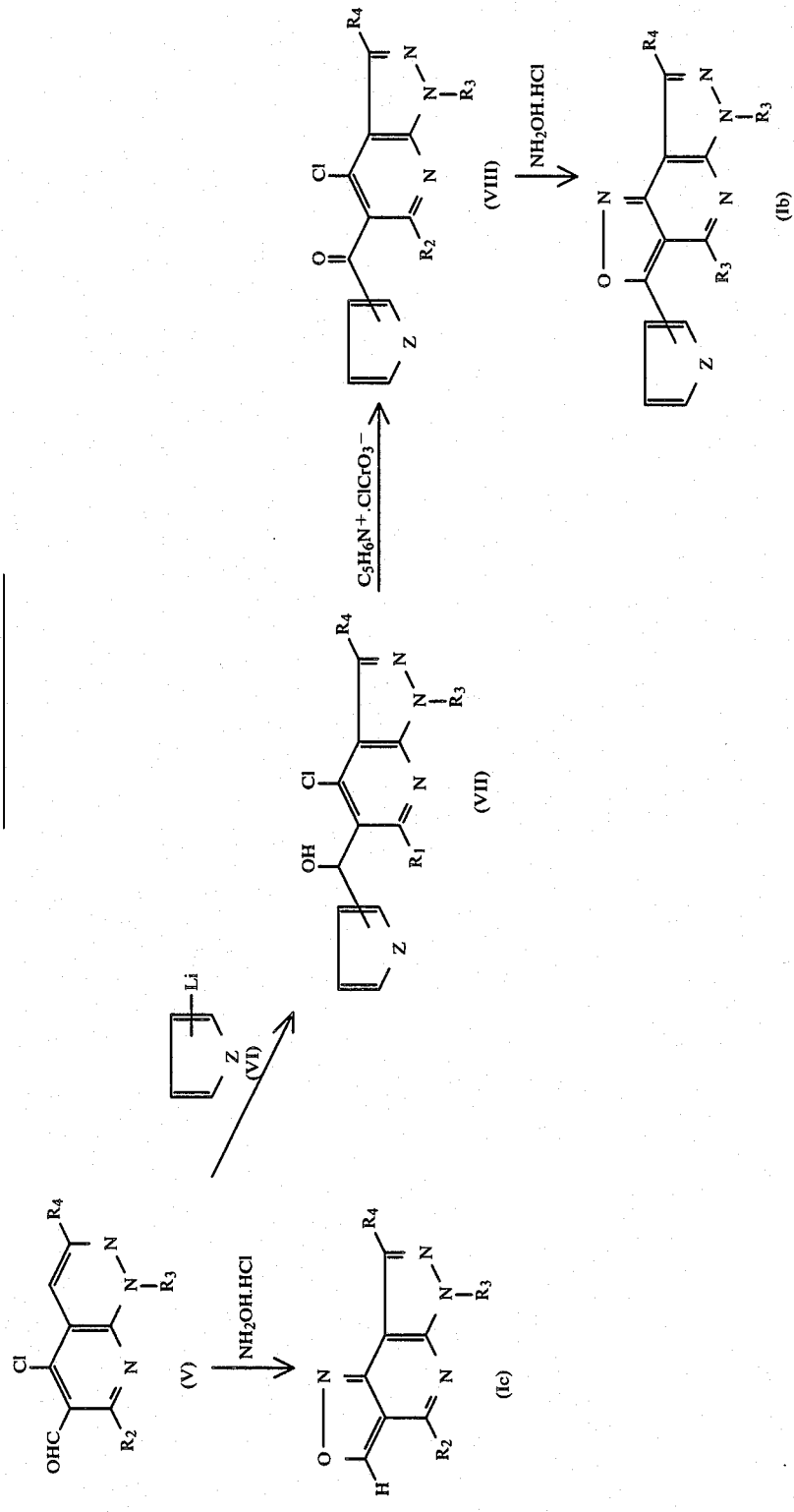

STEP A

Compound III where $R_1$ is not hydrogen or heteroaryl is reacted with hydroxylamine to obtain compound Ia as shown in FIG. 1. This cyclization reaction is typically conducted by refluxing a mixture comprising compound III, hydroxylamine hydrochloride and a suitable solvent such as glacial acetic acid. It is preferable to add to the mixture an acid such as concentrated hydrochloric acid or p-toluenesulfonic acid.

STEP B

Compound II is reduced with $LiAlH_4$ to obtain compound IV as shown in FIG. 1. Typically said reduction is conducted in a suitable medium such as anhydrous tetrahydrofuran, diethyl ether or the like at a temperature of about 0°–30° C.

STEP C

Compound IV is oxidized to compound V with manganese dioxide as shown in FIG. 1. Typically said oxidation is conducted in a suitable medium such as benzene or toluene at a temperature of about 80°–120° C.

STEP D

Compound V is reacted with heteroaryl lithium of formula VI where Z is O, S, $NR_6$ or CH=N, $R_6$ being loweralkyl, phenylloweralkyl or benzenesulfonyl, to obtain compound VII as shown in FIG. 1. When Z is CH=N, the organolithium compound VI is prepared from n-butyl lithium and a bromo compound of the formula

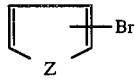

in a suitable solvent such as anhydrous ether at a temperature of between about −70° C. and −50° C. When Z is O, S or $NR_6$, compound VI is prepared from n-butyl lithium and a compound of the formula

in a suitable solvent such as anhydrous ether at a temperature of between about −20° C. and +40° C. Thereafter the solution of compound VI prepared above is added to the solution a solution of compound V in a suitable solvent such as anhydrous tetrahydrofuran and the reaction mixture is stirred at a temperature of between about −10° C. and 10° C.

When Z is benzenesulfonyl substituted nitrogen, 1-benzenesulfonylpyrrole which is used for preparing compound VI can readily be prepared from pyrrolyl anion and benzenesulfonyl chloride by routine procedure.

STEP E

Compound VII is oxidized with pyridinium chlorochromate to obtain compound VIII as shown in FIG. 1. This oxidation is typically conducted by adding pyridinium chlorochromate to a solution of compound VII in a suitable solvent such as dichloromethane and stirring the mixture at a temperature of about 10°–50° C.

STEP F

Compound VIII is reacted with hydroxylamine to obtain compound Ib as shown in FIG. 1. This step is conducted in substantially the same manner as STEP A.

STEP G

Although not indicated in FIG. 1, when the group Z is benzenesulfonyl substituted nitrogen in formula Ib, the benzenesulfonyl group can be converted to hydrogen by hydrolyzing the compound Ib. Said hydrolysis is conducted typically in the presence of NaOH or KOH and a suitable medium such as lower aliphatic alcohol at a temperature of about 80°–120° C.

As a result of STEP F and STEP G, compound I where $R_1$ is a heteroaryl group of the formula

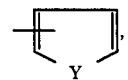

where Y is O, S, $NR_5$ or CH=N, $R_5$ being hydrogen, loweralkyl or phenylloweralkyl are obtained.

STEP H

Compound V is reacted with hydroxylamine to obtain compound Ic as shown in FIG. 1. This step is conducted in substantially the same manner as STEP A above.

STEP I

Where the group $R_1$ in the target compound I is a phenyl group substituted with one or more hydroxy groups, said compound is prepared by first synthesizing the corresponding methoxy substituted compound according to the reaction scheme described above and then converting the methoxy group or groups to hydroxy group or groups by cleavage reaction. Said cleavage reaction is typically conducted by refluxing a mixture comprising the methoxy compound, boron tribormide and a suitable solvent such as 1,2-dichloroethane and thereafter pouring the reaction mixture into ice water.

Compounds (I) of this invention are useful as anxiolytic agents. Anxiolytic activity was determined via direct interaction with benzodiazepin recognition sites in a membrane preparation from rat brain. Table I shows results of activity measurements for some of the compounds of this invention. Details of the procedure is described below:

PROCEDURE

A. Reagents
1. 0.5M Tris Buffer, pH 6.9:
   a. 78.1 g of Tris-HCl diluted to 1 liter
   b. 60.6 g of Tris-base diluted to 1 liter
   c. Adjust pH of Tris-HCl to 6.9 at 25° C. by adding Tris base. (0.5M Tris buffer, pH 6.9)
   d. Make a 1:10 dilution with distilled $H_2O$ (0.05M Tris buffer, pH 6.9)
2. 0.32M sucrose: 21.9 g of sucrose diluted to 200 ml.
3. [Methyl-$^3$H]-Flunitrazepam (70–90 Ci/mmol) is procured from a commercial source.
   For $IC_{50}$ determinations: $^3$H-Flunitrazepam is made up to a concentration of 80 nM and 50 microliter added to each tube (yields a final concentration of 2 nM in the 2 ml assay volume).

4. Clonazepam HCl is obtained from a commercial source.

A stock solution of 0.2 mM is made up in distilled H$_2$O. This is further diluted to 0.1 mM. Twenty micro-liter is added to 3 tubes to determine non specific binding (yields a final concentration of $1\times10^{-6}$M in the assay).

5. Test Compounds:

For most assays, a 1 mM stock solution is made up in a suitable solvent and serially diluted, such that the final concentration in the assay ranges from $10^{-5}$ to $10^{-8}$M. Seven concentrations are used for each assay and higher or lower concentrations may be used, depending on the potency of the drug.

B. Tissue Preparation.

Male Wistar rats are decapitated and the brain rapidly removed. The cerebral cortices are removed, weighed and homogenized with a homogenizer in 20 volumes of ice-cold 0.32M sucrose. This homogenate is centrifuged at 1000 g for 10 minutes, the pellet is discarded and the supernatant is recentrifuged at 30,000 g for 20 minutes. The resulting membrane pellet is resuspended in 40 volumes of 0.05M Tris buffer, pH 6.9.

C. Assay 1 ml 0.05 Tris buffer, pH 6.9
560 micro-liter H$_2$O
70 micro-liter 0.5M Tris buffer, pH 6.9
50 micro-liter $^3$H-Flunitrazepam
20 micro-liter Vehicle (for total binding) or 0.1 mM Clonazepam (for nonspecific binding) or appropriate drug concentrations
300 micro-liter Tissue suspension The tubes containing $^3$H-flunitrazepam, buffer, drugs and H$_2$O are incubated at 0°–4° C. in an ice bath. A 300 micro-liter aliquot of the tissue suspension is added to the tubes at 10-second intervals. The timer is started with the addition to the first tube. The tubes are then incubated for 20 minutes at 0°–4° C. and the assay stopped by vacuum filtration of the samples through Whatman GF/B filters. This step is also done at 10-second intervals. Each filter is immediately rinsed with three 5-ml washes of ice-cold Tris buffer, pH 6.9. Ths filters are counted in 10 ml of Liquiscint counting cocktail. Specific binding is defined as the difference between total binding and binding in the presence of $1\times10^{-6}$M clonazepam. Specific binding is approximately 97% of the total bound ligand. The percent inhibition at each drug concentration is the mean of triplicate determination. IC$_{50}$ claculations are performed using log-probit analysis.

TABLE I

ANXIOLYTIC ACTIVITY

| Compound | $^3$H—Flunitrazepam Binding IC$_{50}$, M |
|---|---|
| 6-Ethyl-3-phenyl-6H—isoxazolo[3,4-d]pyrazolo[3,4-b]pyridine | $4.7 \times 10^{-7}$ |
| 3-(3-Chlorophenyl)-6-ethyl-6H—isoxazolo[3,4-d]pyrazolo[3,4-b]pyridine | $4.4 \times 10^{-6}$ |
| 3-(4-Chlorophenyl)-6-ethyl-6H—isoxazolo[3,4-d]pyrazolo[3,4-b]pyridine | $4.0 \times 10^{-7}$ |
| 6-Ethyl-3-(3-fluorophenyl)-6H—isoxazolo[3,4-d]pyrazolo[3,4-b]pyridine | $2.3 \times 10^{-6}$ |
| 6-Ethyl-3-(4-fluorophenyl)-6H—isoxazolo[3,4-d]pyrazolo[3,4-b]pyridine | $5.3 \times 10^{-7}$ |
| 6-Ethyl-3-(4-tolyl)-6H—isoxazolo[3,4-d]pyrazolo[3,4-b]pyridine | $9.9 \times 10^{-7}$ |
| 6-Ethyl-3-(4-methoxyphenyl)-6H—isoxazolo[3,4-d]pyrazolo[3,4-b]pyridine | $1.2 \times 10^{-6}$ |
| 6-Ethyl-3-(2-methoxyphenyl)-6H—isoxazolo[3,4-d]pyrazolo[3,4-b]pyridine (Prior Art Compound) | $2.0 \times 10^{-6}$ |
| Chlordiazepoxide | $3.4 \times 10^{-7}$ |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stablity, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; and excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution of suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral multiple dose vials made of glass of plastic.

Examples of the compounds of this invention include:
6-Ethyl-3-methyl-6H-isoxazolo[3,4-d]pyrazolo[3,4-b]pyridine;
6-Ethyl-3-phenyl-6H-isoxazolo[3,4-d]pyrazolo[3,4-b]pyridine;
6-Ethyl-3-(3-fluorophenyl)-6H-isoxazolo[3,4-d]pyrazolo[3,4-b]pyridine;
6-Ethyl-3-(4-fluorophenyl)-6H-isoxazolo[3,4-d]pyrazolo[3,4-b]pyridine;
3-(3-Chlorophenyl)-6-ethyl-6H-isoxazolo[3,4-d]pyrazolo[3,4-b]pyridine;
3-(4-Chlorophenyl)-6-ethyl-6H-isoxazolo[3,4-d]pyrazolo[3,4-b]pyridine;
6-Ethyl-3-(2-tolyl)-6H-isoxazolo[3,4-d]pyrazolo[3,4-b]pyridine;
6-Ethyl-3-(3-tolyl)-6H-isoxazolo[3,4-d]pyrazolo[3,4-b]pyridine;
6-Ethyl-3-(4-tolyl)-6H-isoxazolo[3,4-d]pyraozlo[3,4-b]pyridine;
6-Ethyl-3-(4-trifluoromethylphenyl)-6H-isoxazolo[3,4-d]pyrazolo[3,4-b]pyridine;
6-Ethyl-3-(2-methoxyphenyl)-6H-isoxazolo[3,4-d]pyrazolo[3,4-b]pyridine;
6-Ethyl-3-(3-methoxyphenyl)-6H-isoxazolo[3,4-d]pyrazolo[3,4-b]pyridine; and
6-Ethyl-3-(4-methoxyphenyl)-6H-isoxazolo[3,4-d]pyrazolo[3,4-b]pyridine.

The following examples are presented in order to illustrate this invention.

EXAMPLE 1

6-Ethyl-3-methyl-6H-isoxazolo[3,4-d]pyrazolo[3,4-b]pyridine

5-Acetyl-4-chloro-1-ethyl-1H-pyrazolo[3,4-b]pyridine (4.60 g) was refluxed for 2 hours in 450 ml of glacial acetic acid containing 15 g of hydroxylamine hydrochloride and 1.0 g of p-toluenesulfonic acid monohydrate. At the end of this time the reaction volume was reduced to ca. 200 ml under reduced pressure and then it was poured into 800 ml of water. The amorphous precipitate was filtered off and purified over 230–400 mesh silica gel (5% ethyl acetate/dichloromethane). The appropriate fractions were combined and evaporated and the resultant crystalline product was washed with pentane to give 1.75 g, mp 181°–182° C.

ANALYSIS: Calculated for $C_{10}H_{10}N_4O$: 59.39% C; 4.98% H; 27.71% N; Found: 59.45% C; 5.11% H; 27.88% N.

EXAMPLE 2

6-Ethyl-3-phenyl-6H-isoxazolo[3,4-d]pyrazolo[3,4-b]pyridine

5-Benzoyl-4-chloro-1-ethyl-1H-pyrazolo[3,4-b]pyridine (5.0 g) as a slurry in 50 ml of methanol was added to a solution of $H_2NOH$ in 100 ml of methanol prepared by neutralizing 5.0 g of $H_2NOH.HCl$ to a phenolphthalein endpoint. After stirring the mixture overnight the precipitated product was filtered off and dried, amounting to 1.65 g, mp 175°–176°. The filtrate was evaporated and the residue taken up in dichloromethane. After a little insoluble material was filtered off, the residue was chromatographed over silica gel (5% ethyl acetate/dichloromethane) to give fractions containing both the end product and a new, more polar material. A few fractions that contained pure new material were evaporated; the new material was shown by $^1$H-NMR, $^{13}$C-NMR, MS and IR to be the intermediate 5-benzoyl-4-hydroxyamino-1H-pyrazolo[3,4-b]-pyridine. All the fractions containing the end product and this intermediate were evaporated and the residue was refluxed for 1 hour in 50 ml of toluene containing 100 mg of p-toluenesulfonic acid, giving complete conversion to the end product. Workup with $NaHCO_3$/ether gave an additional 0.73 g of the end product, mp 175°–176°. Material for analysis was recrystallized from methanol but the melting point was unchanged.

ANALYSIS: Calculated for $C_{15}H_{12}N_4O$: 68.17% C; 4.58% H; 21.29% N; Found: 68.09% C; 4.57% H; 20.97% N.

EXAMPLE 3

6-Ethyl-3-(3-fluorophenyl)-6H-isoxazolo[3,4-d]pyrazolo[3,4-b]pyridine

4-Chloro-1-ethyl-5-(3-fluorobenzoyl)-1H-pyrazolo[3,4-b]pyridine (4.60 g) and hydroxylamine hydrochloride (14.0 g) were refluxed in a solution of 250 ml of acetic acid and 4 ml of concentrated hydrochloric acid. After 90 minutes, the solvent was evaporated and the residue distributed between dichloromethane and an aqueous sodium bicarbonate solution. The organic phase was evaporated and the residue was chromatographed over 230–400 mesh silica gel (10% ethyl acetate/dichloromethane). Evaporation of the appropriate fractions gave 3.2 g of product, mp 182°–184°. Recrystallization from ethyl acetate gave analytically pure product, mp 183°–184° C.

ANALYSIS: Calculated for $C_{15}H_{11}FN_4O$: 63.82% C; 3.93% H; 19.85% N; Found: 63.75% C; 4.05% H; 19.97% N.

EXAMPLE 4

6-Ethyl-3-(4-fluorophenyl)-6H-isoxazolo[3,4-d]pyrazolo[3,4-b]pyridine

4-Chloro-1-ethyl-5-(4-fluorobenzoyl)-1H-pyrazolo[3,4-b]pyridine (4.5 g) and hydroxylamine hydrochloride (14.0 g) were refluxed in a solution of 250 ml of acetic acid and 4 ml of concentrated hydrochloric acid. After two hours the solvent was evaporated and the residue distributed between dichloromethane and an aqueous sodium bicarbonate solution. The organic phase was evaporated and the residue chromatographed over 230–400 mesh silica gel (10% ethyl acetate/dichloromethane). Evaporation of the appropriate fractions gave 2.2 g of product after trituration with pentane, mp 222°–223° C.

ANALYSIS: Calculated for $C_{15}H_{11}FN_4O$: 63.82% C; 3.93% H; 19.85% N; Found: 64.07% C; 4.07% H; 20.13% N.

EXAMPLE 5

3-(3-Chlorophenyl)-6-ethyl-6H-isoxazolo[3,4-d]pyrazolo[3,4-b]pyridine

4-Chloro-5-(3-chlorobenzoyl)-1-ethyl-1H-pyrazolo[3,4-b]pyridine (2.65 g) was stirred overnight at 90° in 75 ml of glacial acetic acid containing 3.0 g of hydroxylamine hydrochloride. Sodium acetate (3.5 g) was then added, followed by an additional 1.0 g of hydroxylamine hydrochloride. The reaction mixture was then evaporated and the residue distributed between aqueous sodium bicarbonate and dichloromethane. The organic layer was evaporated and the residue was triturated with methanol and then chromatographed (230–400 mesh silica gel, 10% ethyl acetate/dichloromethane) to give 1.20 g of product, mp 207°–209°. It was combined with the products of several other runs and recrystallized from ethyl acetate to give analytically pure material, mp 209°–210° C.

ANALYSIS: Calculated for $C_{15}H_{11}ClN_4O$: 60.31% C; 3.71% H; 18.76% N; Found: 60.06% C; 3.77% H; 18.68% N.

EXAMPLE 6

3-(4-Chlorophenyl)-6-ethyl-6H-isoxazolo[3,4-d]pyrazolo[3,4-b]pyridine

4-Chloro-5-(4-chlorobenzoyl)-1-ethyl-1H-pyrazolo[3,4-b]pyridine (3.76 g) was suspended in 75 ml of glacial acetic acid, and to this was added 1.05 g of hydroxylamine hydrochloride. The reaction mixture was stirred overnight at 80° and the next morning yet another 1.05 g of hydroxylamine hydrochloride was added. After stirring the mixture for additional two hours the solvent was evaporated and the residue washed first with sodium bicarbonate solution and then methanol. The resulting product was then chromatographed over 230–400 mesh silica gel (10% ethyl acetate/dichloromethane), giving 1.51 g of product, mp 248°–250° C.

ANALYSIS: Calculated for $C_{15}H_{11}ClN_4O$: 60.31% C; 3.71% H; 18.76% N; Found 60.16% C; 3.73% H; 19.03% N.

EXAMPLE 7

6-Ethyl-3-(2-tolyl)-6H-isoxazolo[3,4-d]pyrazolo[3,4-b]pyridine

4-Chloro-1-ethyl-5-(2-methylbenzoyl)-1H-pyrazolo[3,4-b]pyridine (5.40 g) was refluxed for 2 hours in 300 ml of glacial acetic acid containing 10 ml of concentrated hydrochloric acid and 10 g of hydroxylamine hydrochloride. At the end of this time the reaction mixture was poured into water and extracted with dichloromethane. The organic phase was washed four times with water and once with saturated sodium bicarbonate solution. It was then evaporated and chromatographed over 230–400 mesh silica gel (10% ethyl acetate/dichloromethane) to give 2.21 g of product, mp 168°–170°. This product was recrystallized from ethyl acetate together with the product of another run to give analytically pure material, mp 170°–171° C.

ANALYSIS: Calculated for $C_{16}H_{14}N_4O$; 69.05% C; 5.07% H; 20.13% N; Found: 68.94% C; 5.15% H; 20.17% N.

EXAMPLE 8

6-Ethyl-3-(3-tolyl)-6H-isoxazolo[3,4-d]pyrazolo[3,4-b]pyridine

4-Chloro-1-ethyl-5-(3-methylbenzoyl)-1H-pyrazolo[3,4-b]pyridine (2.0 g) and hydroxylamine hydrochloride (6.0 g) were suspended in 200 ml of acetic acid, and to this was added 0.5 g of p-toluenesulfonic acid monohydrate. The reaction mixture was refluxed for 2 hours and then distributed between water and dichloromethane. The organic phase was washed four times with water and once with saturated sodium bicarbonate solution. It was then evaporated and chromatographed over 230–400 mesh silica gel, eluting with 10% ethyl acetate/dichloromethane. By combining the appropriate fractions, 1.40 g of product was obtained, mp 178°–179°. This product was combined with the product of another run and recrystallized from ethyl acetate to give product of mp 180°–181° C.

ANALYSIS: Calculated for $C_{16}H_{14}N_4O$: 69.04% C; 5.07% H; 20.13% N; Found: 69.03% C; 5.16% H; 20.33% N.

EXAMPLE 9

6-Ethyl-3-(4-tolyl)-6H-isoxazolo[3,4-d]pyrazolo[3,4-b]pyridine

4-Chloro-1-ethyl-5-(4-methylbenzoyl)-1H-pyrazolo[3,4-b]pyridine (4.40 g) and hydroxylamine hydrochloride (14.0 g) were mixed dry and then suspended in a solution prepared from 200 ml of glacial acetic acid and 5 ml of concentrated hydrochloric acid. The reaction mixture was then brought to reflux with mechanical stirring. After two hours, the reaction was allowed to cool and then the acetic acid was evaporated. The residue was distributed between dichloromethane and an aqueous sodium bicarbonate solution and then the organic phase was dried and evaporated. The crude product was chromatographed over 230–400 mesh silica gel (10% ethyl acetate/dichloromethane). The appropriate fractions were combined, evaporated, and then washed with pentane, giving 2.48 g of product, mp 221°–222° C.

ANALYSIS: Calculated for $C_{16}H_{14}N_4O$: 69.05% C; 5.07% H; 20.13% N; Found: 69.13% C; 5.24% H; 20.41% N.

EXAMPLE 10

6-Ethyl-3-(4-trifluoromethylphenyl)-6H-isoxazolo[3,4-d]pyrazolo[3,4-b]pyridine 4-Chloro-1-ethyl-5-(4-trifluoromethylbenzoyl)-1H-pyrazolo[3,4-b]pyridine (3.10 g) was refluxed for 2 hours in 300 ml of acetic acid containing 9 g of hydroxylamine hydrochloride and 0.6 g of p-toluenesulfonic acid monohydrate. At the end of this time the reaction mixture was poured into water and extracted with dichloromethane. The organic phase was washed well with water, dried, evaporated, and purified by chromatography over 230–400 mesh silica gel (10% ethyl acetate/dichloromethane). In this way, 2.15 g of product was obtained, mp 243°–245°. Recrystallization from ethyl acetate gave analytically pure product, mp 244°–245° C.

ANALYSIS: Calculated for $C_{16}H_{11}F_3N_4O$: 57.83% C; 3.33% H; 16.86% N; Found 58.26% C; 3.32% H; 16.75% N.

EXAMPLE 11

6-Ethyl-3-(2-methyoxyphenyl)-6H-isoxazolo[3,4-d]pyrazolo[3,4-b]pyridine

Five grams of 4-chloro-1-ethyl-5-(2-methoxybenzoyl)-1H-pyrazolo[3,4-b]pyridine was refluxed for 2 hours in 500 ml of acetic acid containing 15 g of hydroxylamine hydrochloride and 1 g of p-toluenesulfonic acid monohydrate. At the end of this time the reaction mixture was poured into water and extracted with dichloromethane. The organic phase was washed well with water, dried, evaporated and chromatographed over 230–400 mesh silica gel. The appropriate fractions were combined and evaporated to give 2.95 g of product, mp 126°–127° C. The melting point was unchanged after recrystallization from ethyl acetate/pentane.

ANALYSIS: Calculated for $C_{16}H_{14}N_4O_2$: 65.29% C; 4.79% H; 19.04% N; Found: 65.63% C; 4.99% H; 19.39% N.

EXAMPLE 12

6-Ethyl-3-(3-methoxyphenyl)-6H-isoxazolo[3,4-d]pyrazolo[3,4-b]pyridine

Five grams of 4-chloro-1-ethyl-5-(3-methoxybenzoyl)-1H-pyrazolo[3,4-b]pyridine was refluxed for 2 hours in 500 ml of acetic acid containing 15 g of hydroxylamine hydrochloride and 1 g of p-toluenesulfonic acid monohydrate. At the end of this time the reaction mixture was poured into water and extracted with dichloromethane. The organic phase was washed well with water, dried, evaporated and chromatographed over 230–400 mesh silica gel. The appropriate fractions were combined and evaporated to give 3.05 g of product, mp 170°–171°. After recrystallization from water it had mp 169°–171° C.

ANALYSIS: Calculated for $C_{16}H_{14}N_4O_2$: 65.29% C; 4.79% H; 19.04% N; Found: 65.44% C; 4.94% H; 19.20% N.

EXAMPLE 13

6-Ethyl-3-(4-methoxyphenyl)-6H-isoxazolo[3,4-d]pyrazolo[3,4-b]pyridine

4-Chloro-1-ethyl-5-(4-methoxy)-1H-pyrazolo[3,4-b]pyridine (4.70 g) was refluxed for 90 minutes in 250 ml of glacial acetic acid containing 15 ml of concentrated hydrochloric acid and 10 g of hydroxylamine hydrochloride. At the end of this time the reaction mixture was poured into water and extracted with dichloromethane. The organic phase was washed four times with water and once with saturated sodium bicarbonate solution. It was then evaporated and chromatographed over 230–400 mesh silica gel (10% ethyl acetate/dichloromethane) to give 2.36 g (54%) of product, mp 215°–216°. This product was recrystallized from ethyl acetate together with the product of another run to give analytically pure material, mp 215°–216° C.

ANALYSIS: Calculated for $C_{16}H_{14}N_4O_2$: 65.29% C; 4.79% H; 19.04% N; Found: 65.24% C; 4.68% H; 19.11% N.

EXAMPLE 14

4-Chloro-1-ethyl-1H-pyrazolo[3,4-b]pyridine-5-carboxaldehyde

Wet $MnO_2$ (110 g) was refluxed for 90 minutes in 1 L of toluene with a Dean-Stark trap for the separation of water. This suspension was then cooled and 4-chloro-1-ethyl-1H-pyrazolo-3,4-b]pyridine-5-methanol (17.5 g) was added in 50 ml of toluene. The reaction mixture was then stirred for 6 hours and filtered with the aid of a filter pad. The toluene was evaporated and the residue added again to 100 g of wet $MnO_2$ freshly prepared in the above manner. After additional 4 hours the reaction was briefly warmed at 55° and then filtered again through a filter pad. The residue which remained after evaporation of the toluene was purified by preparative high performance liquid chromatography (10% ethyl acetate/hexane, 250 ml/min) to yield 11.70 g of 4-chloro-1-ethyl-1H-pyrazolo[3,4-b]pyridine-5-carboxaldehyde, mp 89°–90° C.

ANALYSIS: Calculated for $C_9H_8ClN_3O$: 51.56% C; 3.85% H; 20.05% N; Found: 51.18% C; 3.79% H; 19.84% N.

I claim:

1. A compound having the formula

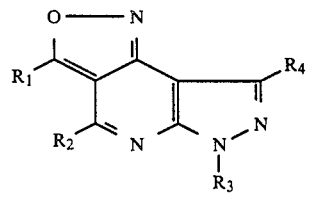

where $R_1$ is hydrogen, loweralkyl, arylloweralkyl, aryl or heteroaryl; $R_2$ is hydrogen or loweralkyl; $R_3$ is loweralkyl, loweralkoxyloweralkyl, cycloalkyl, arylloweralkyl or heteroarylmethyl; and $R_4$ is hydrogen or loweralkyl; the term aryl signifying an unsubstituted phenyl group or a phenyl group substituted with 1, 2 or 3 substituents each of which being independently a loweralkyl group, loweralkoxy group, hydroxy group, trifluoromethyl group, chlorine or fluorine, with the proviso that the aryl group shall not have chlorine or fluorine at the ortho position, the term heteroaryl signifying a group having the formula

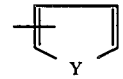

where Y is O, S, $NR_5$ or CH=N, $R_5$ being hydrogen, loweralkyl or phenylloweralkyl, and the term cycloalkyl signifying a cycloalkyl group of 3 to 7 carbon atoms.

2. The compound as defined in claim 1, where $R_3$ is loweralkyl.

3. The compound as defined in claim 2, where $R_3$ is ethyl.

4. The compound as defined in claim 1, where $R_4$ is hydrogen.

5. The compound as defined in claim 2, where $R_4$ is hydrogen.

6. The compound as defined in claim 3, where $R_4$ is hydrogen.

7. The compound as defined in claim 1, where $R_2$ is hydrogen.

8. The compound as defined in claim 2, where $R_2$ is hydrogen.

9. The compound as defined in claim 3, where $R_2$ is hydrogen.

10. The compound as defined in claim 1, where $R_1$ is loweralkyl or aryl.

11. The compound as defined in claim 2, where $R_1$ is loweralkyl or aryl.

12. The compound as defined in claim 3, where $R_1$ is loweralkyl or aryl.

13. The compound as defined in claim 1, where $R_1$ is loweralkyl or aryl, $R_2$ is hydrogen, $R_3$ is loweralkyl and $R_4$ is hydrogen.

14. The compound as defined in claim 1, which is 6-ethyl-3-methyl-6H-isoxazolo[3,4-d]pyrazolo[3,4-b]pyridine.

15. The compound as defined in claim 1, which is 6-ethyl-3-phenyl-6H-isoxazolo[3,4-d]pyrazolo[3,4-b]pyridine.

16. The compound as defined in claim 1, which is 6-ethyl-3-(3-fluorophenyl)-6H-isoxazolo[3,4-d]pyrazolo[3,4-b]pyridine.

17. The compound as defined in claim 1, which is 6-ethyl-3-(4-fluorophenyl)-6H-isoxazolo[3,4-d]pyrazolo[3,4-b]pyridine.

18. The compound as defined in claim 1, which is 3-(3-chlorophenyl)-6-ethyl-6H-isoxazolo[3,4-d]pyrazolo[3,4-b]pyridine.

19. The compound as defined in claim 1, which is 3-(4-chlorophenyl)-6-ethyl-6H-isoxazolo[3,4-d]pyrazolo[3,4-b]pyridine.

20. The compound as defined in claim 1, which is 6-ethyl-3-(2-tolyl)-6H-isoxazolo[3,4-d]pyrazolo[3,4-b]pyridine.

21. The compound as defined in claim 1, which is 6-ethyl-3-(3-tolyl)-6H-isoxazolo[3,4-d]pyrazolo[3,4-b]pyridine.

22. The compound as defined in claim 1, which is 6-ethyl-3-(4-tolyl)-6H-isoxazolo[3,4-d]pyrazolo[3,4-b]pyridine.

23. The compound as defined in claim 1, which is 6-ethyl-3-(4-trifluoromethylphenyl)-6H-isoxazolo[3,4-d]pyrazolo[3,4-b]pyridine.

24. The compound as defined in claim 1, which is 6-ethyl-3-(2-methoxyphenyl)-6H-isoxazolo[3,4-d]pyrazolo[3,4-b]pyridine.

25. The compound as defined in claim 1, which is 6-ethyl-3-(3-methoxyphenyl)-6H-isoxazolo[3,4-d]pyrazolo[3,4-b]pyridine.

26. The compound as defined in claim 1, which is 6-ethyl-3-(4-methoxyphenyl)-6H-isoxazolo[3,4-d]pyrazolo[3,4-b]pyridine.

27. An anxiolytic composition comprising an effective anxiety alleviating amount of the compound as defined in claim 1 and a carrier therefor.

28. A method of treating a patient in need of relief from anxiety which comprises administering to the patient an effective anxiety alleviating amount of the compound as defined in claim 1.

29. A method of preparing a compound of the formula

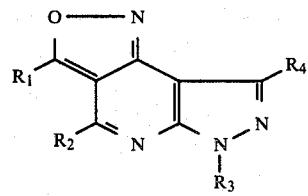

where $R_1$ is hydrogen, loweralkyl, arylloweralkyl, aryl or heteroaryl; $R_2$ is hydrogen or loweralkyl; $R_3$ is loweralkyl, loweralkoxyloweralkyl, cycloalkyl, arylloweralkyl or heteroarylmethyl; and $R_4$ is hydrogen or loweralkyl; the term aryl signifying an unsubstituted phenyl group or a phenyl group substituted with 1, 2 or 3 substituents each of which being independently a loweralkyl group, loweralkoxy group, hydroxy group, trifluoromethyl group, chlorine or fluorine, with the proviso that the aryl group shall not have chlorine or fluorine at the ortho position, the term heteroaryl signifying a group having the formula

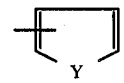

where Y is O, S, $NR_5$ or CH=N, $R_5$ being hydrogen, loweralkyl or phenylloweralkyl, and the term cycloalkyl signifying a cycloalkyl group of 3 to 7 carbon atoms, which comprises reacting a compound of the formula

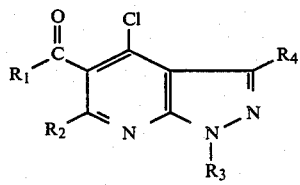

with hydroxylamine to obtain said compound.

* * * * *